United States Patent [19]

Sykes et al.

[11] Patent Number: 4,752,469

[45] Date of Patent: Jun. 21, 1988

[54] POTENTIATORS OF BETA-LACTAM ANTIBIOTICS

[75] Inventors: Richard B. Sykes, Belle Mead; J. Scott Wells, Ringoes; Raymond Cooper, Old Bridge, all of N.J.

[73] Assignee: E. R. Squibb & Sons, Inc., Princeton, N.J.

[21] Appl. No.: 569,106

[22] Filed: Jan. 9, 1984

[51] Int. Cl.⁴ .......................................... A61K 35/70
[52] U.S. Cl. ................................. 424/117; 424/115
[58] Field of Search ............................. 424/117, 115

Primary Examiner—Jerome D. Goldberg
Attorney, Agent, or Firm—Lawrence S. Levinson; Donald J. Barrack

[57] ABSTRACT

Cultivation of the microorganism *Chromobacterium violaceum* A.T.C.C. No. 31532 yields two novel compounds which have been designated SQ 28,504 and SQ 28,546 in addition to EM5117, a previously disclosed antibacterial compound.

2 Claims, 5 Drawing Sheets

FIGURE I
INFRARED SPECTRUM OF SQ 28,504 IN POTASSIUM BROMIDE

INFRARED SPECTRUM OF SQ 28,546 IN POTASSIUM BROMIDE

100MHz 13C NMR SPECTRUM OF SQ 28,546 IN DEUTERATED WATER

POTENTIATORS OF BETA-LACTAM ANTIBIOTICS

BACKGROUND OF THE INVENTION

United Kingdom patent application No. 2,071,650, published Sept. 23, 1981 discloses the biological production of an antibiotic designated EM5117 ((R)-3-(acetylamino)-3-methoxy-2-oxo-1-azetidinesulfonic acid) by the cultivation of the microorganism Chromobacterium violaceum A.T.C.C. No. 31532.

SUMMARY OF THE INVENTION

It has been found that cultivation of *Chromobacterium violaceum* A.T.C.C. No. 31532 yields two novel compounds which have been designated SQ 28,504 and SQ 28,546 in addition to EM5117. SQ 28,504 and SQ 28,546 enhance the antibacterial activity of β-lactam antibiotics against gram-negative bacteria. Additionally, SQ 28,546 has antibacterial activity in its own right.

DETAILED DESCRIPTION OF THE INVENTION

The Microorganism

Figure 1:
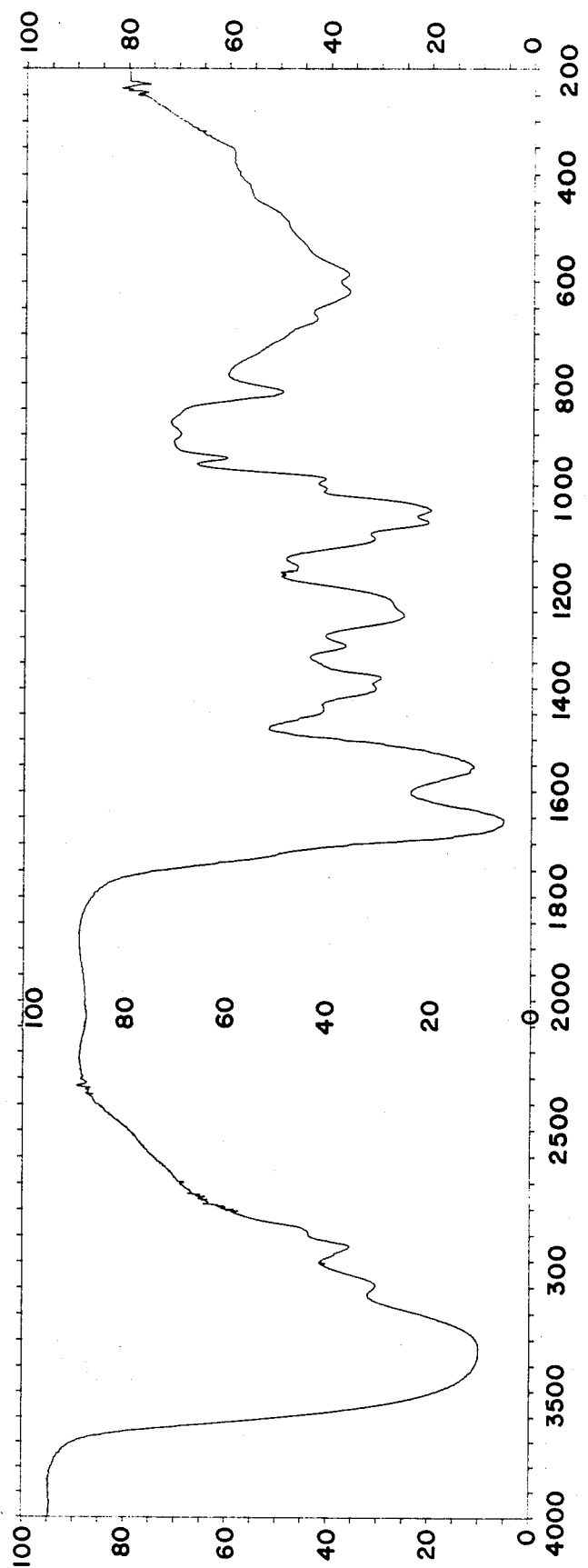
FIG. 1 shows the infrared spectrum of SQ 28,504 in potassium bromide.

The microorganism used for the production of SQ 28,504 and SQ 28,546 is a strain of *Chromobacterium violaceum*. A subculture of the microorganism can be obtained from the permanent collection of the American Culture Type Collection, Rockville, Md. Its accession number in the repository is A.T.C.C. No. 31532. In addition to the specific microorganism described and characterized herein, it should be understood that mutants of the microorganism (e.g., mutants produced through the use of x-rays, ultraviolet radiation or nitrogen mustards) can also be cultured to produce SQ 28,504 and SQ 28,546.

*Chromobacterium violaceum* SC 11,378, A.T.C.C. No. 31532 can be isolated from a moist soil sample containing the microorganism by first stamping the soil sample on a medium containing:

| | |
|---|---|
| Soil Extract | 400 ml |
| Distilled Water | 600 ml |
| Yeast Extract | 5.0 g |
| Glucose | 10.0 g |
| Agar | 17.5 g |

The medium is adjusted to pH 6.0 and sterilized in an autoclave at 121° C. for 20 minutes. After 24 to 72 hours incubation at 25° C., colonies of *Chromobacterium violaceum* are isolated from the plated soil. These isolated colonies are then grown on a medium containing:

| | |
|---|---|
| Yeast Extract | 1 g |
| Beef Extract | 1 g |
| NZ amine A | 2 g |
| Glucose | 10 g |
| Agar | 15 g |
| Distilled water | to 1 liter |

The medium is adjusted to pH 7.3 and autoclaved at 121° C. for 30 minutes.

*Chromobacterium violaceum* is a gram negative rod often showing barring, bipolar staining and lipid inclusions. It is motile by a single polar flagellum with occassional lateral flagella which are smaller in size.

On nutrient agar *Chromobacterium violaceum* produces violet colonies. The pigment is enhanced on media rich in tryptophane and yeast extract. In nutrient broth it produces a violet ring on the wall of the tube but no confluent pellicle. The violet pigment is soluble in ethanol but insoluble in water and chloroform.

*Chromobacterium violaceum* is mesophilic, growing over a range of 15°–37° C.; no growth occurs at 4° C. or above 37° C. Casein is hydrolyzed strongly by the microorganism, which is oxidase positive. In the presence of *Chromobacterium violaceum*, glucose, fructose and trehalose are fermented (method of Hugh & Leifson, 1953). L-Arabinose is not utilized by the microorganism either fermentatively or oxidatively. Hydrogen cyanide is produced by the microorganism and aesculin hydrolysis is negative.

The above-described key characteristics provide the basis for the identification of the microorganism as *Chromobacterium violaceum* as distinguished from *Chromobacterium lividum*, the only other species of the genus Chromobacterium recognized in the 8th edition of Bergey's Manual of Determinative Bacteriology.

Production of SQ 28,504 and SQ 28,546

*Chromobacterium violaceum* A.T.C.C. No. 31532 produces compounds SQ 28,504 and SQ 28,546, each of which potentiates the antibiotic activity of several β-lactam antibiotics, e.g., aztreonam, ampicillin, piperacillin and moxalactam. To form the potentiators according to the preferred method, *Chromobacterium violaceum* A.T.C.C. No. 31532 is grown at, or near, room temperature (25° C.) under submerged aerobic conditions in an aqueous, nutrient medium containing an assimilable carbohydrate and nitrogen source. The fermentation is carried out for approximately 18 to 30 hours, preferrably about 24 hours, at the end of which time the potentiators have been formed.

After the fermentation has been completed, the broth supernate is adjusted to pH 8.5 and the active materials are adsorbed onto Amberlite IRA-458 resin* in the OH$^-$ form. The resin is separated from the spent aqueous and packed in a glass column. The active materials are eluted from the resin with dilute acetic acid. Further purification is accomplished by chromatography on Dowex 50W-X2 resin* in the H$^+$ form, followed by chromatography of the active fractions on Sephadex G-10 resin. Separation of the two active components is accomplished by chromatography on Bio-Rad AG 1-X2 resin* (acetate form) with an acetic acid gradient in aqueous pyridine. Final purification of SQ 28,504 is achieved by sequential chromatographic treatments on Bio-Rad AG 50W-X2 resin**** (pyridinium form), cellulose and finally on Bio-Rad AG 50W-X2 resin in the pyridinium form. Final purification of SQ 28,546 is achieved by sequential chromatographic treatments on Bio-Rad AG 50W-X2 (pyridinium form) resin and cellulose.

*Amberlite IRA-458 resin is a strongly basic gel type ion exchange resin with acrylic matrix and quaternary ammonium functionality, manufactured by Rohm & Haas Company, Philadelphia, Pa.
*Dowex 50W-X2 resin is a strongly acidic gel type ion exchange resin with a styrene-divinylbenzene matrix and benzenesulfonic acid functionality manufactured by Dow Chemical Company, Midland, Mich.
**Sephadex G-10 resin is cross-linked dextran gel beads manufactured by Pharmacia Fine Chemicals AB, Uppsala, Sweden.
***Bio-Rad AG1-X2 resin is a strongly basic gel type ion exchange resin with a styrene-divinylbenzene matrix and quaternary ammonium functionality manufactured by Bio-Rad Laboratories, Richmond, Calif.
****Bio-Rad AG 50W-X2 resin is a strongly acidic gel type ion exchange resin with a styrene-divinylbenzene matrix and benzenesulfonic acid functionality manufactured by Bio-Rad Laboratories, Richmond, Calif.

The following examples further illustrate the production and isolation of SQ 28,504 and SQ 28,546.

EXAMPLE 1

Production and Isolation of SQ 28,504 and SQ 28,546

*Chromobacterium violaceum* A.T.C.C. No. 31532 was maintained on the following medium:

|  | Grams |
| --- | --- |
| Yeast extract | 1.0 |
| Beef extract | 1.0 |
| NZ Amine A | 2.0 |
| Glucose | 10.0 |
| Agar | 15.0 |
| Distilled water | to 1 liter |

The pH was adjusted to 7.3 and the medium was then sterilized at 121° C. for 30 minutes.

A loopful of surface growth from an agar slant of the above medium was used to inoculate each of five 500 ml Erlenmeyer flasks containing 100 ml each of the following medium:

|  | Grams |
| --- | --- |
| Oatmeal | 20.0 |
| Tomato paste | 20.0 |
| Tap water | to 1 liter |

The pH was adjusted to 7.0 and the medium was then sterilized at 121° C. for 15 minutes.

After inoculation, the flasks were incubated at 25° C. on a rotary shaker (300 rpm; 2 inch throw) for 24 hours. A 1% (vol/vol) transfer was made from the grown culture flasks to a 75 liter Fermatron fermentor (New Brunswick Scientific, Edison, N.J.), containing 50 liters of the following sterilized medium:

|  | Grams |
| --- | --- |
| Glucose | 25.0 |
| Yeast extract | 2.0 |
| NZ Amine A | 4.0 |
| Tap water | to 50 liters |

The pH was adjusted to 7.0 before sterilization at 121° C. for 15 minutes. After inoculation, the fermentation was carried on for 24 hours at 25° C., with an agitation rate of 200 rpm and an air flow of 50 liters per minute. At harvest, the contents of the tank were centrifuged, yielding approximately 49 liters of broth supernate. To this broth supernate, adjusted to pH 8.5 with sodium hydroxide, was added one liter of Amberlite IRA-458 resin, OH− form. After stirring at room temperature for 1.5 hours, the supernate was removed by decantation. The resin, washed with 5 liters of dissolved water, was loaded into a column and eluted with 2 liters of aqueous 2% acetic acid. The eluate was concentrated to dryness in vacuo, and the resulting residue, dissolved in 100 ml of distilled water, was chromatographed on a 5 cm×41 cm column of Dowex 50W-X2(H+) 50-100 mesh. The active components, eluted with 10% aqueous pyridine, were pooled and concentrated in vacuo to dryness. The residue was dissolved in 30 ml of distilled water and chromatographed on Sephadex G-10 (5 cm×102 cm column) with a methanol-water (9:1) mixture. The active fractions were pooled and concentrated to 10 ml in vacuo. This concentrate, adjusted to pH 9 with pyridine, was then chromatographed on a 1.5 cm×56 cm column of Bio-Rad AG1-X2 (acetate form) resin, 200–400 mesh, with one liter of a linear gradient of 0 to 1.2M acetic acid in 10% aqueous pyridine. SQ 28,504 was eluted with ca. 0.3M acetic acid, while SQ 28,546 eluted later. The fractions comprising each peak were pooled, and each pool was concentrated in vacuo to a dry residue that was subsequently redissolved in 2 ml of 1M formic acid.

The formic acid solution of SQ 28,504 was applied to a 1.5 cm×55 cm column of Bio-Rad AG 50W-X2 (pyridinium form) resin, 200 to 400 mesh, and eluted with one liter of a linear gradient of 0 to 0.5M pyridine in 1M formic acid. The activity eluted with ca. 0.2M pyridine. Active fractions were pooled, concentrated to dryness in vacuo and the residue was dissolved in 2 ml of distilled water. This solution was chromatographed on 2.5 cm×52 cm column of Whatman Cellulose CC31 with 1.2 liters of an acetonitrile-water linear gradient (9:1 to 1:1). The active fractions, eluted with approximately 70% acetonitrile, were pooled and concentrated to dryness in vacuo. The residue, after being dissolved in 1 ml of 1M acetic acid, was chromatographed on a 1 cm×10 cm column of Bio-Rad AG 50W-X2 (pyridinium form) resin 200–400 mesh. SQ 28,504 was eluted with 1M pyridine-acetic acid. Removal of the solvent and subsequent lyophilization from water yielded 8 mg of SQ 28,504 as a colorless solid.

EXAMPLE 2

Isolation of SQ 28,504 and SQ 28,546

Four 50-liter fermentations were run as described in Example 1. Broth supernates from each were treated with 1-liter portions of Amberlite IRA-458 (OH− form). The loaded resin was pooled and, after being washed with 8 liters of distilled water, was loaded into a column. Elution with 2% aqueous acetic acid (8 liters) recovered the activity. The active fractions were pooled and concentrated in vacuo to 100 ml, and chromatographed on a column (5 cm×41 cm) of Dowex 50W-X2 resin in the H+ form, 50 to 100 mesh. The activity was eluted with 10% aqueous pyridine. The active fractions were pooled and concentrated to dryness in vacuo. The resulting residue was dissolved in 30 ml of distilled water and chromatographed on a Sephadex G-10 column (5 cm×102 cm) with a mixture of methanol-water (9:1). The eluted, active fractions were again pooled and concentrated to 10 ml. This concentrate, adjusted to pH 9 with pyridine, was chromatographed on a column (2.5 cm×56 cm) of Bio-Rad AG1-X2 (acetate form) resin, 200 to 400 mesh, with a linear gradient of 1.25M aqueous pyridine to 3M pyridine-1.25M acetic acid. Approximately 3.6 liters of eluting solvent was used. SQ 28,504 eluted at ca. 0.3M acetic acid while SQ 28,546 eluted at ca. 0.5M acetic acid. Fractions containing SQ 28,546 were pooled and concentrated in vacuo to dryness, and the residue was chromatographed on Bio-Rad AG50W-X2 (pyridinium form) resin in a 2.5 cm×30 cm column. The activity was recovered by elution with 1 liter of a linear gradient of 0 to 0.5M pyridine in 1M formic acid. Fractions containing SQ 28,546, eluted with ca. 0.25M pyridine, were pooled and concentrated in vacuo to dryness. The residue, dissolved in 2 ml of distilled water, was chromatographed on a 2.5 cm×29 cm column of Whatman Cellulose CC31, eluting with an acetonitrile-water gradient (9:1 to 1:1, 1 liter). The active fractions were pooled and the solvents were removed in vacuo. Subsequent lyophilization yielded 56 mg of SQ 28,546 as a colorless solid.

ANALYTIC DATA

SQ 28,504

UV ($H_2O$): No absorption maxima above 200 nm I.R. (KBr) (see FIG. 1): 3400 (broad) 1650 (broad) $cm^{-1}$.

FAB-M.S.: $(M+H)^+$, m/z 964 and $(M-H)^-$, m/z 962, indicating a molecular weight of 963

Electrophoresis:

| Buffer | pH | Mobility* |
|---|---|---|
| formic acid:acetic acid:water (1:3:6) | 1.8 | −0.20 |
| 0.05M $NaH_2PO_4$ | 4.5 | 0.00 |
| sodium 0.05M phosphate | 7.0 | +0.30 |
| sodium 0.05M carbonate-bicarbonate | 9.2 | +0.60 |

*Mobility on Whatman CHR 20 paper after 1 hour at 12.5 V/cm. Mobilities are relative to vitamin $B_{12}$ (0.00) and p-nitrobenzenesulfonate anion (1.00).

T.L.C.: Silica gel 60F-254 (Merck) n-propanol-$NH_4OH$ (7:3) $R_f=0.3$.

Color Reactions: Rydon, ninhydrin and fluram positive.

Acid hydrolysis products: serine(1), threonine(1), lysine(1), $SO_4^{--}$ and unidentified components.

SQ 28,546

Figure 3:
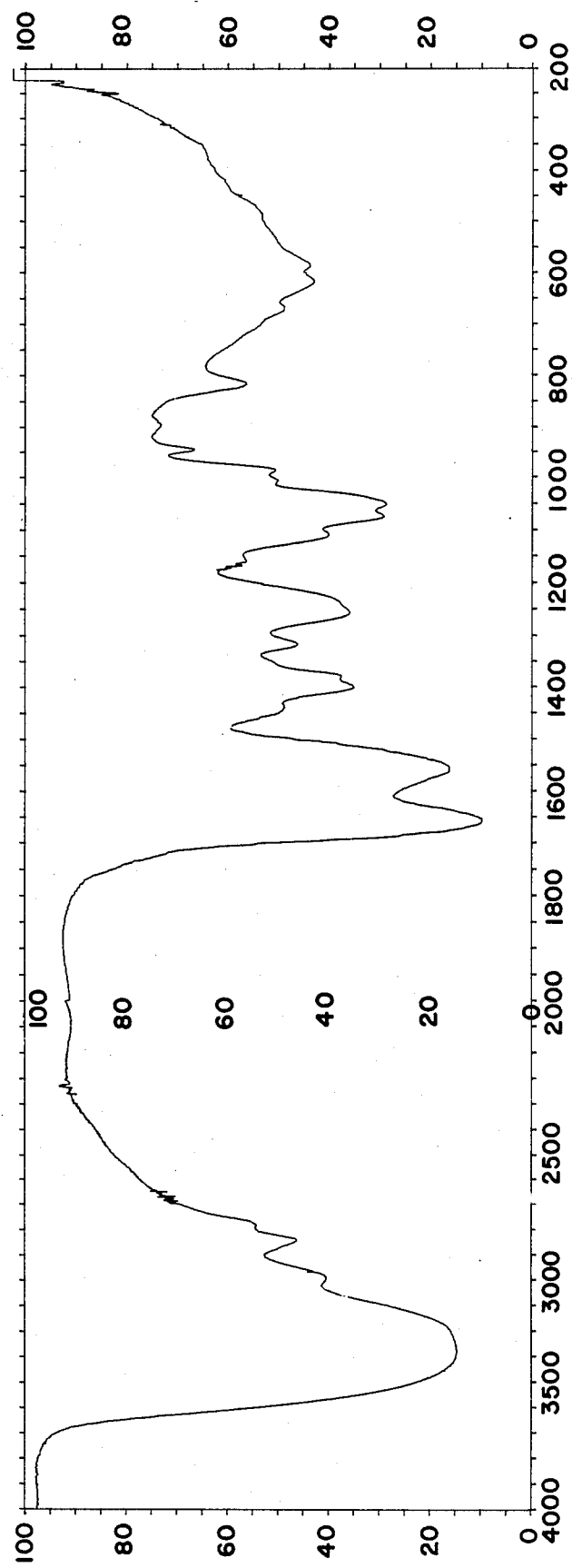
FIG. 3 shows the infrared spectrum of SQ 28,546 in potassium bromide.

UV: No absorption maxima above 200 nm I.R. (KBr) (see FIG. 3): 3400 (broad) and 1650 $cm^{-1}$.

FAB-M.S.: $(M+H)^+$, m/z 1180

Elemental Analysis: Found C: 42.43%, H: 6.91%, N: 10.59%, S: 2.57%.

T.L.C.: Silica Gel 60F-254 (Merck), n-propanol-$NH_4OH$ 7:3 $R_f=0.2$

Color Reactions: Rydon, ninhydrin and fluram positive.

Electrophoresis:

| Buffer | pH | Mobility* |
|---|---|---|
| formic acid:acetic acid:water (1:3:6) | 1.8 | −0.20 |
| 0.05M $NaH_2PO_4$ | 4.5 | 0.00 |
| sodium 0.05M phosphate | 7.0 | +0.30 |
| sodium 0.05M carbonate-bicarbonate | 9.2 | +0.60 |

*Mobility on Whatman CHR 20 paper after 1 hour at 12.5 V/cm. Mobilities are relative to vitamin $B_{12}$ (0.00) and p-nitrobenzenesulfonate anion (1.00).

Acid hydrolysis products: serine (2), threonine (1), glutamic acid (1), lysine (1), $SO_4^{--}$ and unidentified components.

Figure 5:
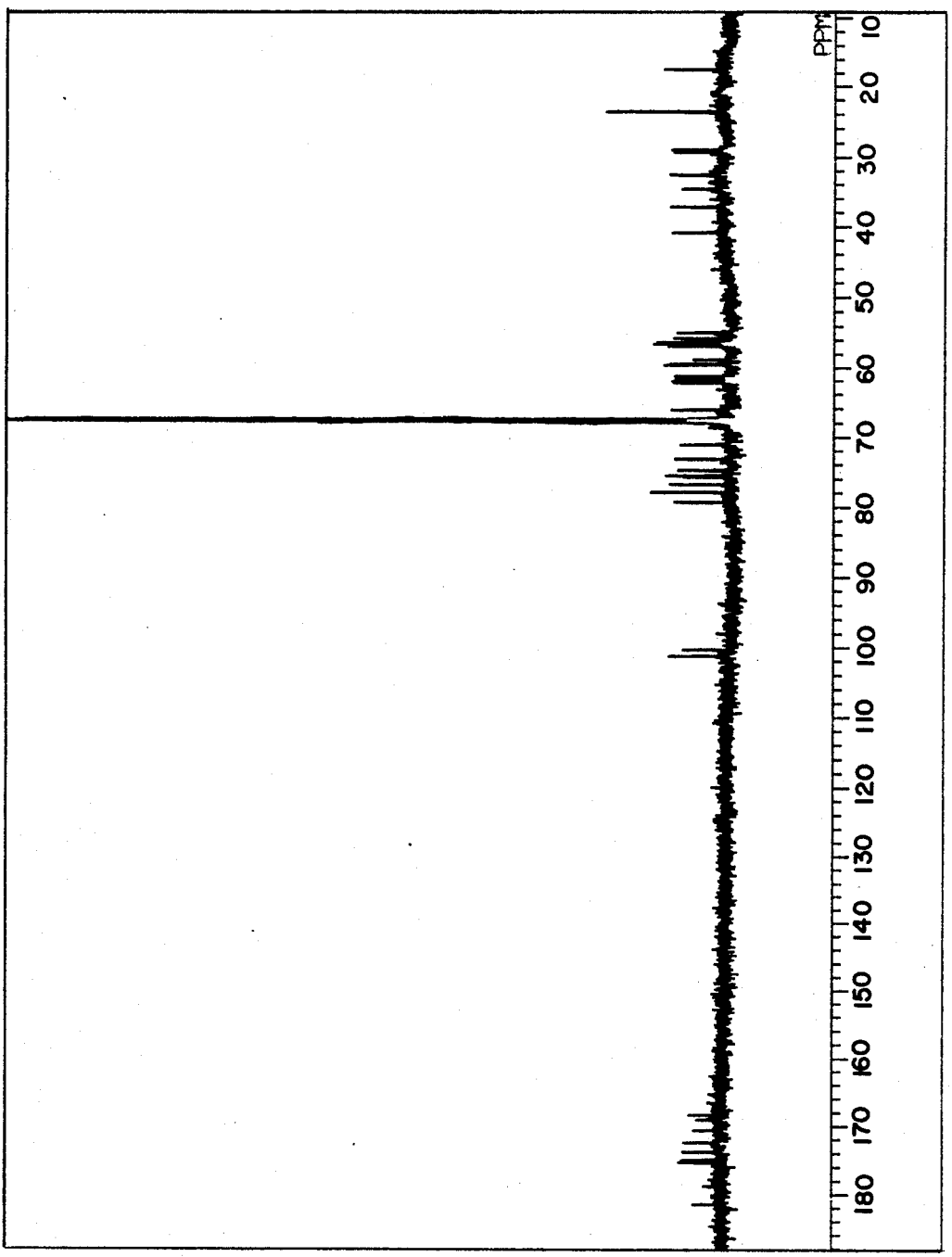
FIG. 5 shows the 100 MHz $^{13}$C-NMR spectrum of SQ 28,546 in deuterated water.

$^{13}C$-NMR spectrum (deuterated water) (see FIG. 5): S 181.5, 178.8, 175.3, 175.0, 173.8, 172.4, 170.6, 169.1, 168.4, 101.3, 100.3, 79.3, 77.9, 76.7, 75.7, 75.5, 74.7, 73.1, 71.0, 66.1, 62.2, 62.0, 61.8, 61.6, 61.2, 59.6, 59.4, 58.8, 56.5, 56.2, 55.6, 54.8, 40.8, 37.1, 34.5, 32.5, 29.1, 28.8, 23.5, 23.5, 17.4 ppm.

BIOLOGICAL ACTIVITY

Both SQ 28,504 and SQ 28,546 potentiate the activity of β-lactam antibiotics vs. *Escherichia coli* and *Proteus rettgeri*. Moreover, the potentiation occurs with cell wall synthesis inhibitors other than β-lactams in the *Proteus rettgeri* system. Potentiation of β-lactam antibiotics has been described for bulgecin by Imada et al. (J. Antibiotics 35: 1400–1403, 1982; Pct. Int. Appl. WO 8300, 148, 20 January 1983; JP Appl. 81/106.55407, 07 July 1981).

Gram negative organisms with closed or blocked porin channels may present a clinical problem because of the inability of β-lactam antibiotics to penetrate the membrane to reach their target sites. The compounds of this invention can aid β-lactam antibiotics to penetrate the cell membrane, and they are, therefore, useful adjuvants in therapy.

The technique used was the double disk diffusion test, described by D. J. Krogstad and R. C. Moellering, Jr. in: Antibiotics in Laboratory Medicine, ed. V. Lorian, pps. 298–341, Williams and Wilkins, 1980. Disks contained 30 μg of compound, and unless noted otherwise, were placed adjacent to each other on the surface of a nutrient agar seeded with a test organism in a Petri dish. Augmentation of the zones of inhibition of a number of cell wall synthesis inhibitors in the presence of the test compounds was observed, such augmentation being evidence for potentiation of the antibiotic activity.

The results are shown in the following tables:

| (30 μg/ Disc) Plus | μg/Disc or Units/ Disc if noted | Interaction[1] *Escherichia coli* SC 8294[2] | *Proteus rettgeri* SC 8479[2] |
|---|---|---|---|
| SQ 28,504 | | | |
| Aztreonam | 30 | E | E |
| Ampicillin | 10 | E | E |
| Cephalothin | 30 | I | E |
| Cefamandole | 30 | E | E |
| Cefotaxime | 30 | E | E |
| Cefoxitin | 30 | I | E |
| Penicillin G | 100 Units | E | E |
| Piperacillin | 30 | E | E |
| Mecillinam | 10 | I | E |
| Moxalactam | 30 | E | E |
| N—f-thienamycin | 30 | I | E |
| Fosfonomycin | 30 | E | E |
| Diumycin | 30 | E | E |
| SQ 28,546 | | | |
| Aztreonam | 30 | E | E |
| Cephalothin | 30 | I | E |
| Cefamandole | 30 | I | E |
| Cefotaxime | 30 | I | E |
| Cefoxitin | 30 | I | E |
| Penicillin G | 100 Units | I | E |
| Ampicillin | 10 | E | E |
| Piperacillin | 30 | E | E |
| Azocillin | 30 | I | E |
| Mecillinam | 10 | I | E |
| Moxalactam | 30 | E | E |
| N—f-thienamycin | 30 | I | E |
| Vancomycin | 30 | I | I |
| Fosfonomycin | 30 | I | E |

| (30 μg/ Disc) Plus | μg/Disc or Units/ Disc if noted | Interaction[1] | |
|---|---|---|---|
| | | *Escherichia coli* SC 8294[2] | *Proteus rettgeri* SC 8479[2] |
| Diumycin | 30 | I | E |

[1] I = Indifference
E = Enhancement of Activity

[2] Culture Collection of E. R. Squibb & Sons. Inc., Princeton, New Jersey.

SQ 28,546 also possesses antibacterial activity, as shown by conventional agar-dilution assays.

| Organism | SC #[1] | MIC (μg/ml) |
|---|---|---|
| *Staphylococcus aureus* | SC 1276 | >100 |
| *Proteus mirabilis* | SC 3855 | 25 |
| *Proteus rettgeri* | SC 8479 | 12.5 |
| *Proteus vulqaris* | SC 9416 | 12.5 |
| *Salmonella typhosa* | SC 1195 | 25.0 |

[1] Culture Collection of E. R. Squibb & Sons, Inc., Princeton, New Jersey.

Figure 2:
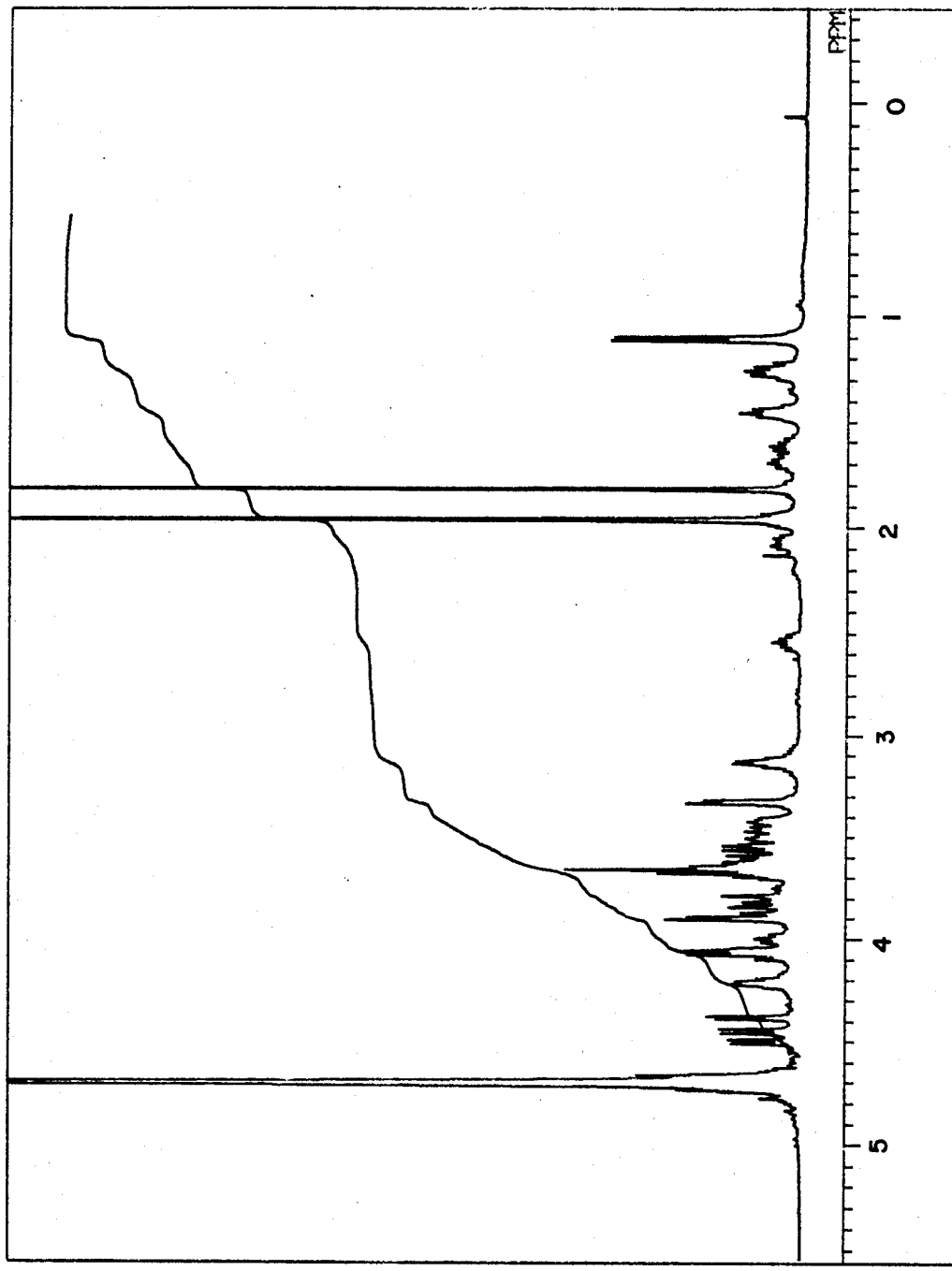
FIG. 2 shows the 400 MHz $^1$H-NMR spectrum of SQ 28,504 in deuterated water.

What is claimed is:

1. SQ 28,504; having a molecular weight of about 963; having an infrared spectrum as in FIG. 1; and having a 400 MHz $^1$H-NMR as in FIG. 2.

Figure 4:
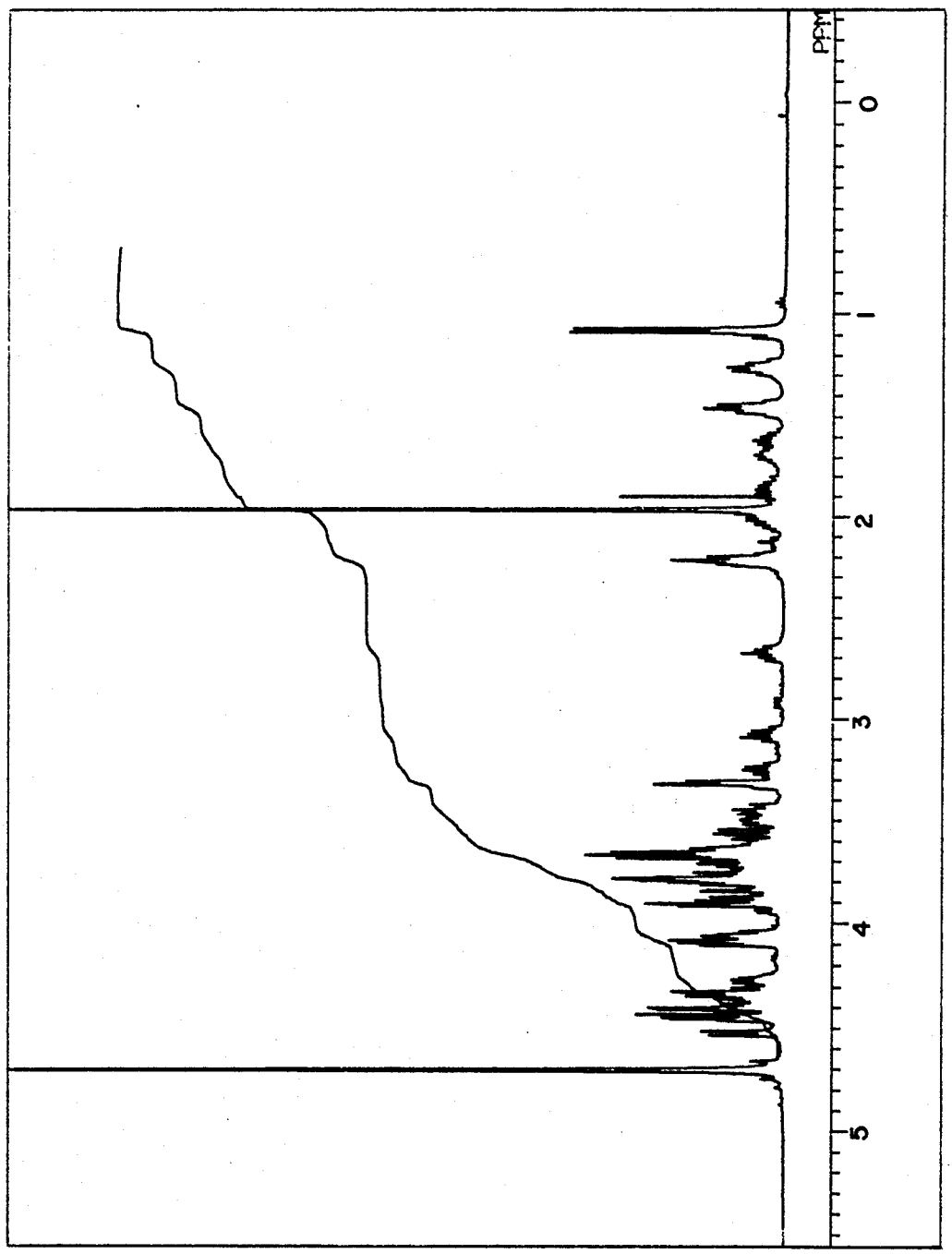
FIG. 4 shows the 400 MHz $^1$H-NMR spectrum of SQ 28,546 in deuterated water.

2. SQ 28,546; having an approximate elemental analysis of C, 42.43%, H, 6.91%, N, 10.59% and S, 2.57%; having an infrared spectrum as in FIG. 3; having a 400 MHz $^1$H-NMR spectrum as in FIG. 4; and having a 100 MHz $^{13}$C-NMR spectrum as in FIG. 5.

* * * * *